United States Patent [19]

Heinecke et al.

[11] Patent Number: 5,520,629
[45] Date of Patent: May 28, 1996

[54] COMBINED ADHESIVE STRIP AND TRANSPARENT DRESSING DELIVERY SYSTEM

[75] Inventors: Steven B. Heinecke, New Richmond, Wis.; Donald G. Peterson, Shoreview, Minn.

[73] Assignee: Minnesota Mining and Manufacturing Company, St. Paul, Minn.

[21] Appl. No.: 932,616

[22] Filed: Aug. 20, 1992

Related U.S. Application Data

[62] Division of Ser. No. 681,120, Apr. 5, 1991, Pat. No. 5,160,315.

[51] Int. Cl.$^6$ ........................................ A61F 13/00
[52] U.S. Cl. ........................... 602/57; 602/58; 604/180; 206/441
[58] Field of Search ........................... 128/849, 853, 128/854, 888, 887; 602/57, 58, 41, 42; 604/180, 307; 206/440, 441

[56] References Cited

U.S. PATENT DOCUMENTS

| | | | |
|---|---|---|---|
| 3,899,077 | 8/1975 | Spiegelberg | 206/441 |
| 4,094,316 | 6/1978 | Nathanson | 602/42 |
| 4,499,896 | 2/1985 | Heinecke | 128/156 |
| 4,600,001 | 7/1986 | Gilman | 604/307 |
| 4,614,183 | 9/1986 | McCracken et al. | 128/132 R |
| 4,669,458 | 6/1987 | Abraham et al. | 123/133 |
| 4,743,232 | 5/1988 | Kruger | 604/180 |
| 4,753,232 | 6/1988 | Ward | 602/57 |
| 4,832,008 | 5/1989 | Gilman | 206/440 |
| 4,884,563 | 12/1989 | Sessions | 128/155 |
| 4,917,112 | 4/1990 | Kalt | 128/888 |
| 5,018,516 | 5/1991 | Gilman | 128/155 |
| 5,035,687 | 7/1991 | Sandbank | 604/180 |
| 5,061,258 | 10/1991 | Martz | 604/307 |
| 5,160,315 | 11/1992 | Heinecke et al. | 602/58 |

FOREIGN PATENT DOCUMENTS

| | | |
|---|---|---|
| 0051935 | 5/1982 | European Pat. Off. . |
| 0161865 | 11/1985 | European Pat. Off. . |
| 0303422 | 2/1989 | European Pat. Off. . |

*Primary Examiner*—Paul B. Prebilic
*Attorney, Agent, or Firm*—Gary L. Griswold; Walter N. Kirn; Dale A. Bjorkman

[57] ABSTRACT

A system for delivering both adhesive strips and transparent dressings to a patient. The adhesive strip or strips are provided with tab means for enhanced handleability and easy removal of the adhesive strip, and are releasably adhered directly to either the release liner or carrier layer of the transparent dressing. Preferably, the tab means is an integral part of one of the layers provided for delivery of the thin film dressing. Specifically, either the release liner or the carrier layer is provided as separately removable portions, and the adhesive strip is attached to the release liner or the carrier layer across the adjoining edge of these portions to allow removal of one portion from the balance of the composite at a time. When one portion is so removed, the adhesive strip is also removed and remains attached to that removed portion. The adhesive strip may then be easily handled for delivery to the desired site on the patient.

7 Claims, 5 Drawing Sheets

COMBINED ADHESIVE STRIP AND TRANSPARENT DRESSING DELIVERY SYSTEM

This is a division of application Ser. No. 07/681,120 filed Apr. 5, 1991 now U.S. Pat. No. 5,160,315.

FIELD OF INVENTION

The present invention relates to pressure-sensitive adhesive composites comprising a backing coated on one side with adhesive. More particularly, it relates to pressure-sensitive adhesive composites having improved means for handling and application to a surface. The invention is of particular benefit in the application of backings which are very thin, adhesive-coated transparent films widely used as medical dressings.

BACKGROUND

Transparent dressings are widely used as a protective layer over wounds and catheterization sites.

Oftentimes, adhesive strips are used in conjunction with transparent dressings to provide closure for wound sites or to secure catheter tubes, etc. Adhesive strips of this type are commercially available, for example, from 3M as Steri-Strip™ adhesive strips. Other such tapes include foam tapes, Micropore™ tape, Transpore™ tape and a whole host of assorted medical tapes. Because these products are used together so often, it would be desirable to find an efficient dispensing system to provide both products in a rapid and efficient manner.

A transparent dressing currently available on the market is the Op-Site™ I.V. 3000 dressing. This transparent dressing is adhered to a release liner, and has removal tabs provided along the entire length of opposite ends of the dressing to allow easy removal from the liner. The removal tabs themselves are removed from the dressing either by peeling away from the transparent film, or by tearing the film along the edge corresponding to the removal tabs. When the film is torn in this way, a strip of adhesive coated film about 1 cm. wide remains that is releasably adhered to the removal tab. This adhesive-coated film strip does not have a tab means or an intentionally provided overhanging edge to afford easy removal from the removal tab. The adhesive-coated strip may be peeled off of the removal tab for use as a separate adhesive strip.

Con Med™ Inc. provides a product for securing catheters called the Venigard Jr.™ dressing. This product comprises a transparent membrane having a foam border. Accessory foam strips for further securing of the catheter are releasably adhered to the same side of a single liner sheet as the membrane. No tab means are provided to assist in removal of the accessory foam strips from the liner.

Bioclusive™ dressing, the Johnson & Johnson transparent dressing product, utilizes a three-part liner delivery system as disclosed in U.S. Pat. No. 4,614,183 to McCracken. The central liner piece of the commercial embodiment of this dressing bears a "piggy-back" style adhesive label for recording patient information on the opposite side of the release liner from the transparent film. This label does not have a tab means to assist in removal from the liner.

SUMMARY OF THE INVENTION

The wound treatment composite of the present invention provides a system for delivering both adhesive strips and transparent dressings to a patient. In one aspect of this invention, a thin film backing at least partially coated on one surface with a pressure-sensitive adhesive has a release liner releasably adhered to the adhesive coated surface of the backing. One or more adhesive strips are releasably adhered to the release liner on the opposite surface of the release liner from the backing. The adhesive strip or strips are provided with tab means for enhanced handleability and easy removal of the adhesive strip from the release liner.

In another aspect of this invention, a wound treatment composite is provided wherein a thin film backing at least partially coated on one surface with a pressure-sensitive adhesive has a release liner releasably adhered to the adhesive coated surface of the backing. A carrier layer having top and bottom faces is releasably adhered at the bottom face to the surface of the backing opposite the surface containing the pressure-sensitive adhesive, with the carrier layer being attached to the backing more tenaciously than the release liner is adhered to the adhesive-coated surface of the backing. One or more adhesive strips are releasably adhered to the top face of the carrier layer. The adhesive strip or strips are provided with tab means for enhanced handleability and to facilitate removal of the adhesive strip from the release liner.

The tab means to enhance handleability and removal of the adhesive strips from the rest of the composite may be separate paper or plastic tabs releasably adhered to one end of the adhesive strip. Where more than one adhesive strip is provided in the composite, the tab means may be individual pieces of paper or plastic tabs releasably adhered to each adhesive strip, or may be a single paper or plastic tab releasably adhered to all strips at once. Preferably, the tab means is an integral part of one of the layers provided for delivery of the thin film dressing. Specifically, either the release liner or the carrier layer is provided as separately removable portions, and the adhesive strip is releasably adhered to the release liner across the adjoining edge of these portions to allow removal of one portion from the balance of the composite at a time. When one portion is so removed, the adhesive strip is also removed and remains attached to that removed portion. The adhesive strip then has free ends that are readily available for grasping by the user for delivery of the adhesive strip to the desired site on the patient. The release liner or carrier is provided as separately removable portions by separation means that may be a continuous-cut line, a perforation line or the like.

In the case where the adhesive strip or strips are releasably adhered to the carrier layer, the carrier layer is preferably divided into separately removable portions by a continuous-cut line for easy separation. Where the adhesive strip or strips are releasably adhered to the release liner, the release liner may be divided by a continuous-cut line or by perforations. Perforations are particularly desirable because in converting the composite, additional care is needed on the adhesive coated side of the backing to insure no separation of the liner that would expose the adhesive to contamination or problems with undesirable adhesion to the processing equipment or package.

The described wound treatment composite provides in one unit the necessary components to treat many wounds and veni-puncture sites. These materials are provided in a compact package, reducing the amount of wasteful packaging of wound treatment components and enhancing the convenience and availability of the components to the user. Because all materials are provided in one package, the practitioner may realize a time savings as compared to opening multiple packages for a single procedure. Additionally, the provision of both adhesive strips and transparent dressings in a single package will encourage their use in combination. One of the combination protocols for wound treatment comprises first using an adhesive strip to close the wound, and then covering both the wound and the adhesive strip with a transparent dressing. The transparent dressing, in addition to providing stability to the wound site, affords protection to the wound from exposure to bacteria, liquid moisture and other undesirable external factors. This wound treatment protocol is believed to be highly beneficial for protecting a wound site, yet currently underutilized in the health care profession.

DESCRIPTION OF DRAWING

Figure 1:
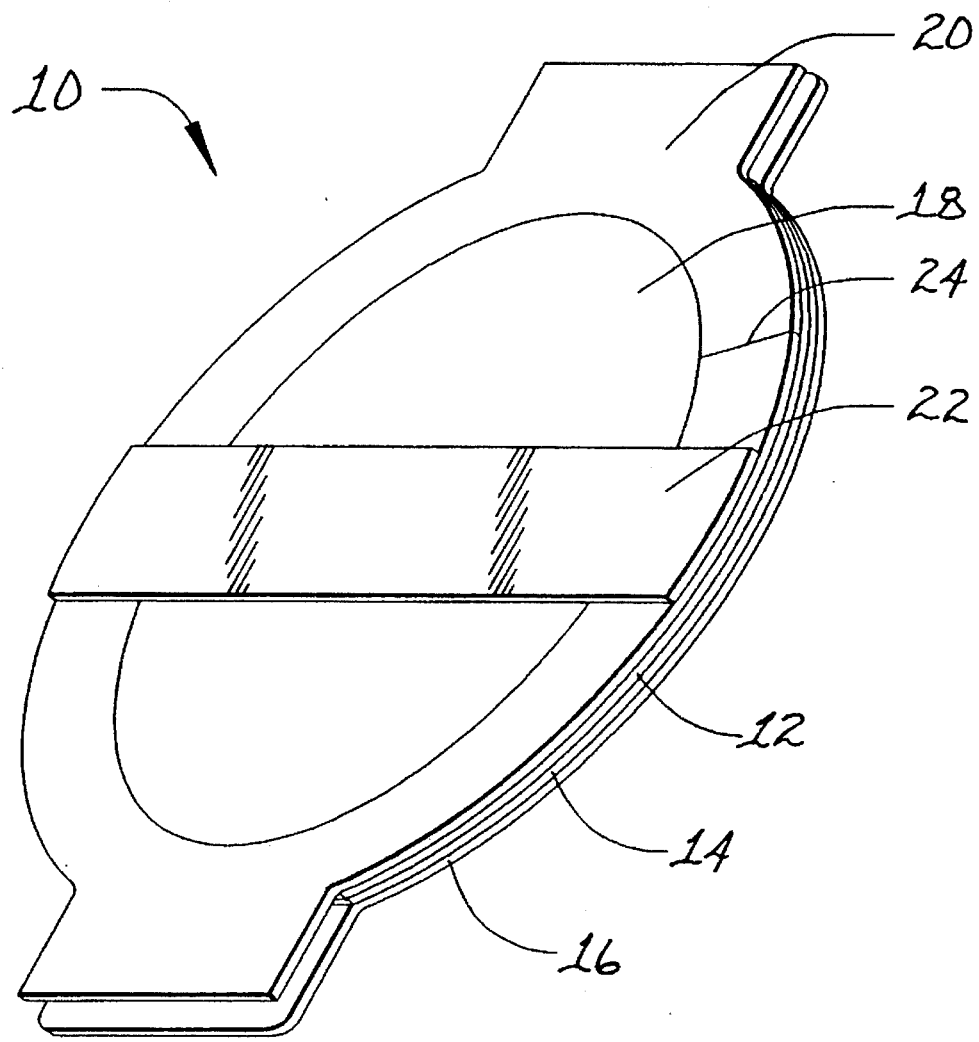
FIG. 1 is a perspective view of an elliptical shaped wound treatment composite of the present invention.

FIG. 1 is a perspective view of elliptical wound treatment composite 10. This shape of wound treatment composite has been found to contour well to the patient's body. Elliptical wound treatment composite 10 comprises backing 12 coated with pressure-sensitive adhesive 14. Liner 16 covers pressure-sensitive adhesive 14. Carrier window 18 and carrier frame 20 provide support and rigidity to flimsy backing 12. Adhesive strip 22 is releasably adhered to carrier window 18 and carrier frame 20. Score line 24 is provided in carrier frame 20 to facilitate separation and removal of carrier frame 20 from backing 12.

Figure 2A:
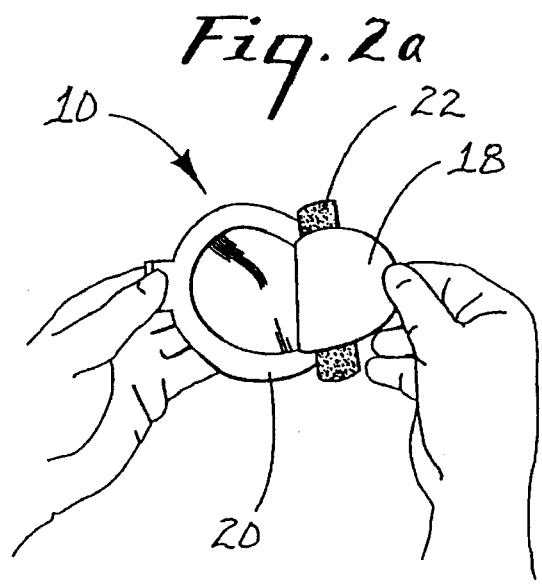
FIGS. 2 a,b,c, and d are plan views showing the method of applying the elliptical shaped wound treatment composite of FIG. 1.
Figure 2B:
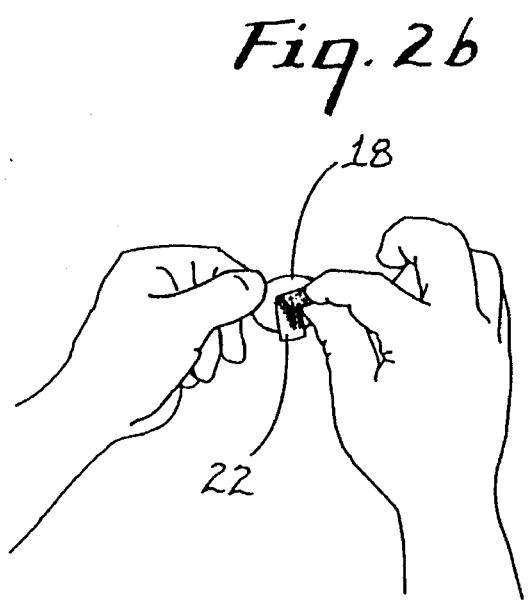
Figure 2C:
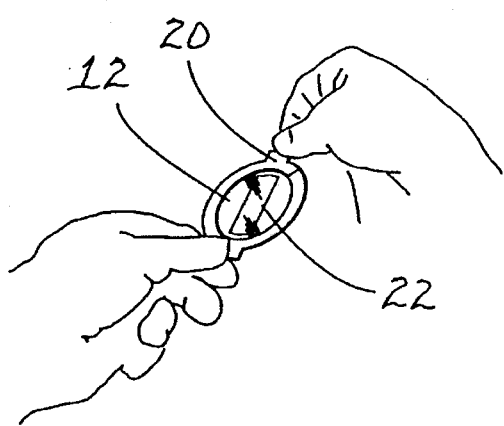
Figure 2D:
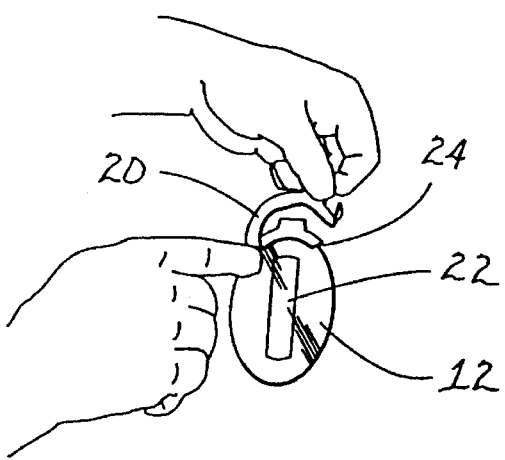

FIGS. 2a, b, c, and d illustrate the method of delivering components of wound treatment composite 10 of FIG. 1, wherein like numerals identify like parts. As shown in FIG. 2a, carrier window 18 is first removed, thereby also removing adhesive strip 22 from elliptical wound treatment composite 10. As shown in FIG. 2b, the user then removes adhesive strip 22 from carrier window 18 by grasping adhesive strip 22 at either end that was once adhered to carrier frame 20. Adhesive strip 22 is then applied to the appropriate site on the patient, for example to close an incision or wound. Liner 16 is then peeled away from pressure-sensitive adhesive coated backing 12 in preparation to be applied to the patient. FIG. 2c illustrates the placement of elliptical wound treatment composite 10 on the site to be protected on the patient by holding carrier frame 20 and looking through transparent backing 12. Backing 12 is optionally placed directly over adhesive strip 22, thereby providing maximum protection to the wound site. Finally, FIG. 2d illustrates the removal of carrier frame 20 from backing 12 by separating at score line 24 and peeling carrier frame 20 away.

Figure 3:
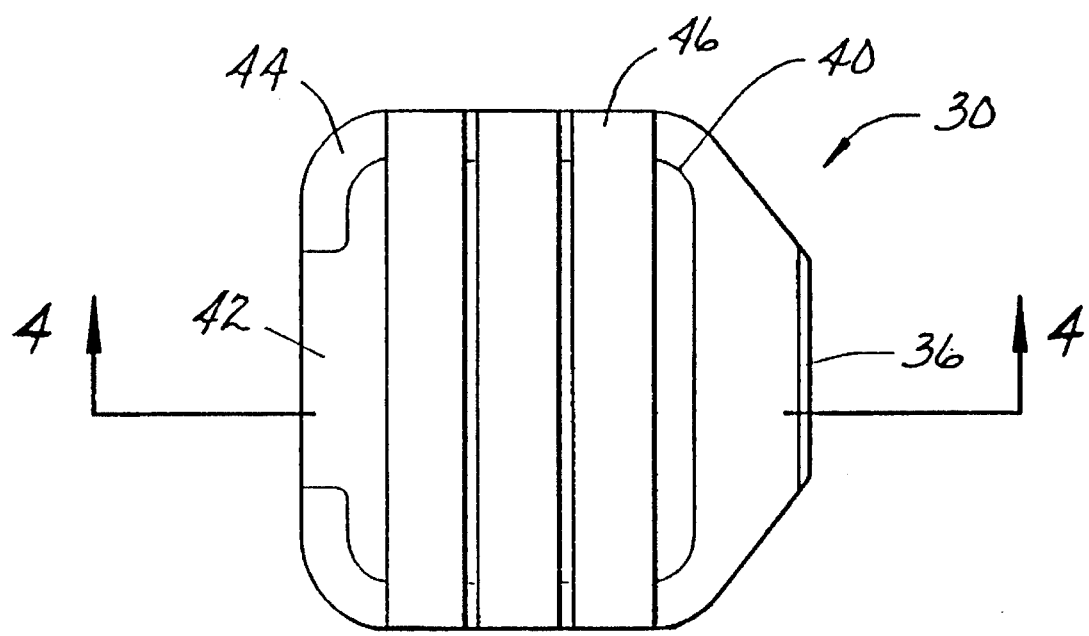
FIG. 3 is a plan view of a wound treatment composite according to the present invention.
Figure 4:
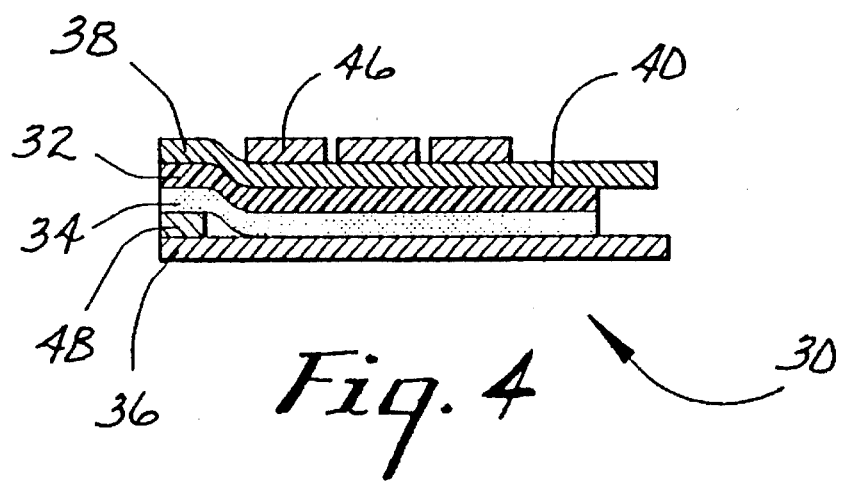
FIG. 4 is a cross-sectional view of the wound treatment composite of FIG. 3 taken along line 4—4 of FIG. 3.

FIG. 3 and FIG. 4 are a plan view and a cross-sectional view, respectively, of wound treatment composite 30 of the present invention, where like numerals designate like parts. Film backing 32 is made of a thin transparent polymeric film which is moisture vapor permeable and liquid and bacteria impermeable, such as a polyester or polyurethane film. Pressure-sensitive adhesive 34 is an adhesive exhibiting low irritation to the skin, preferably a hypoallergenic acrylate copolymer adhesive. Adhesive 34 covers at least a portion of backing 32, and here is illustrated to cover the entire bottom of the film. Release liner 36 is releasably adhered to adhesive 34, and is removed immediately before applying backing 32 to a substrate. Carrier 38 is cut at score line 40 to provide separately removable carrier window portion 42 and carrier frame portion 44. Adhesive strips 46 are releasably adhered to the top face of carrier 38. In use, carrier window portion 42 is first removed from wound treatment composite 30, simultaneously removing adhesive strips 46 from the composite. After removal from wound treatment composite 30, adhesive strips 46 extend beyond carrier window portion 42, and are readily available for grasping by the user and applying adhesive strips 46 to the skin of a patient or any other desired substrate. In this manner, a wound may first be closed using adhesive strips 46, or a catheter tube or the like may be secured. Liner 36 is then removed from adhesive coated backing 32 by the user, and wound treatment composite 30 is then located over the site to be protected. Catheter support strip 48 is optionally located at one side of wound treatment composite 30, thereby providing special reinforcement and securement means for tubing extending from a veni-puncture area or the like.

Figure 5:
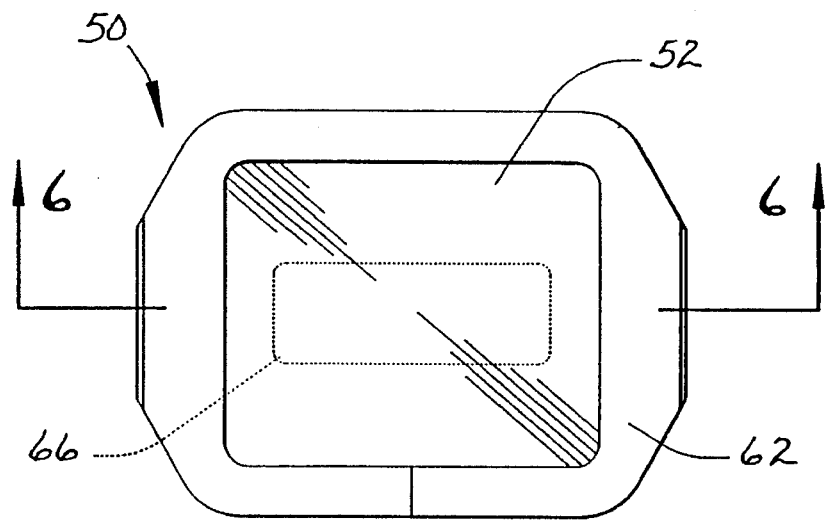
FIG. 5 is a plan view of a wound treatment composite of the present invention.
Figure 6:
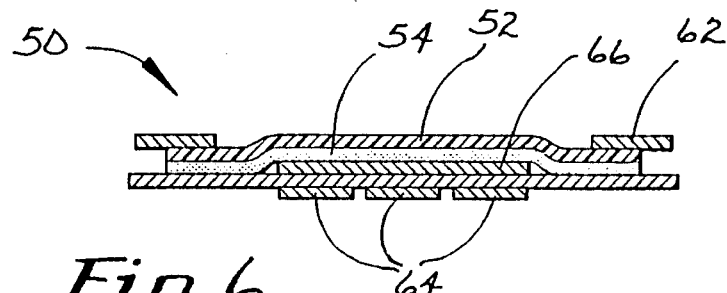
FIG. 6 is a cross-sectional view of the wound treatment composite of FIG. 5 taken along line 6—6 of FIG. 5.
Figure 7:
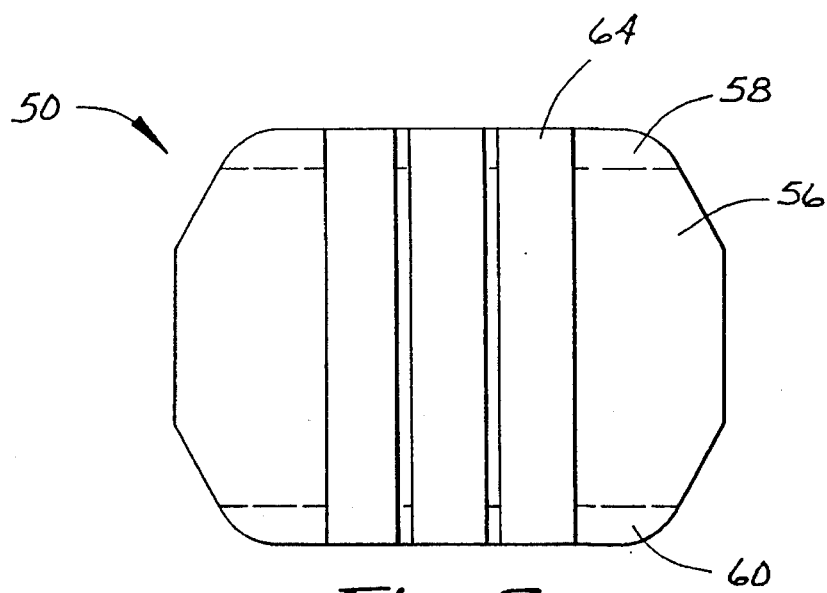
FIG. 7 is a plan view of the wound treatment composite of FIG. 5 shown from the opposite side of the wound treatment composite.

FIGS. 5 and 7 are top and bottom views of wound treatment composite 50 and FIG. 6 is a cross-sectional view of wound treatment composite 50 taken along line 6—6 of FIG. 5. Wound treatment composite 50 comprises film backing 52 coated on one surface with pressure-sensitive adhesive 54. Central liner portion 56 and side liner portions 58 and 60 cover pressure-sensitive adhesive 54. Central liner portion 56 and side liner portions 58 and 60 are separated by either a perforation line or continuous score lines in the liner material. Perforation lines may advantageously be used to avoid difficulties in separation of liner portions during the converting process. Carrier frame 62 provides rigidity and support for the flimsy backing 52. Adhesive strips 64 are releasably adhered to central liner portion 56 and side liner portions 58 and 60. Absorbent pad 66 is optionally provided in the center of backing 52 on the same side as pressure-sensitive adhesive 54. In use, the user has the choice of either first removing the central liner portion 56, thereby exposing the end portions of adhesive strips 64, or alternatively removing either side liner portion 58 or 60, or both, thereby exposing at least the central portion of adhesive strips 64. Wound treatment composite 50 is then set aside, pressure-sensitive adhesive 54 side face up, during application of adhesive strips 64 to the desired location on the patient. Remaining liner portions 56, 58 and/or 60 are then removed from adhesive coated backing 52, and adhesive coated backing 52 is then applied to the desired location on the patient.

Figure 8:
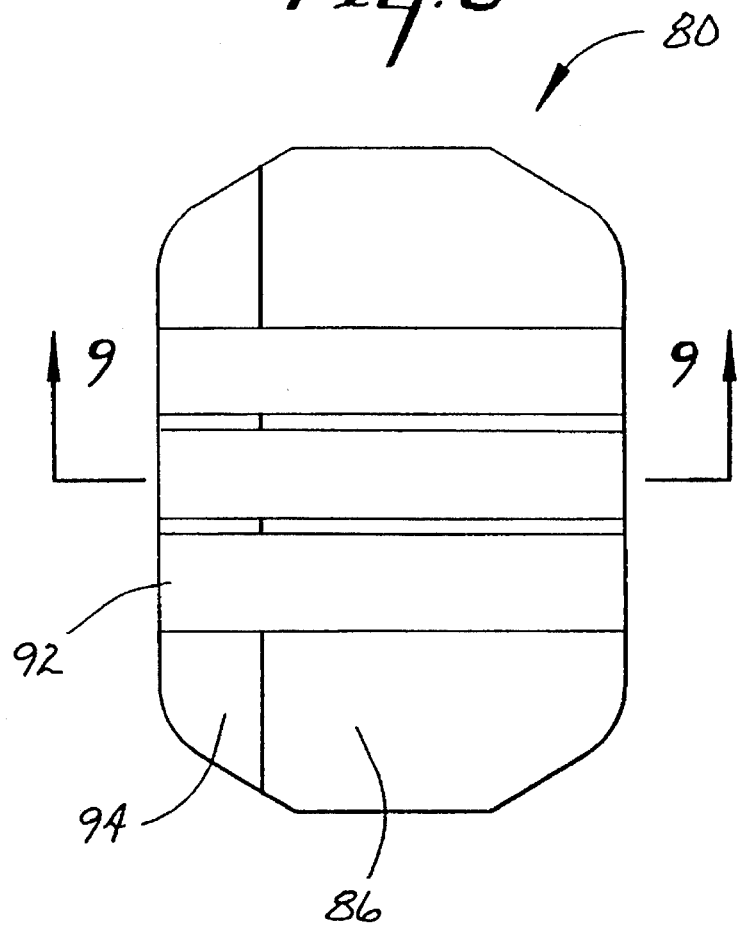
FIG. 8 is a plan view of an alternative embodiment of the wound treatment composite of the present invention having tab means to facilitate separation of adhesive strips from the transparent dressing.
Figure 9:
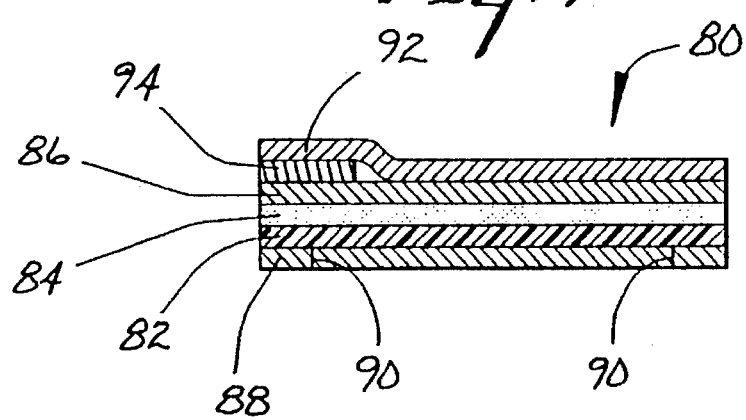
FIG. 9 is a cross-sectional view of the wound treatment composite of FIG. 8, taken along line 9—9.

FIG. 8 is a plan view, and FIG. 9 is a cross-sectional view taken along line 9—9 in FIG. 8, of wound treatment composite 80, wherein like numerals identify like parts. Transparent film 82 is coated with pressure-sensitive adhesive 84, which in turn is laminated to release liner 86. Carrier layer 88 is optionally provided on the opposite side of backing 82 from adhesive 84 to provide enhanced stability and to prevent wrinkling of backing 82 during application to the skin. Optional score line 90 in carrier layer 88 allows separation of a carrier window portion from a carrier frame portion as discussed in detail above. Adhesive strips 92 are releasably adhered to release liner 86 on the surface opposite the adhesive coated backing 82. Tab 94 is releasably adhered to adhesive strips 92 at one end to facilitate removal of adhesive strips 92 from release liner 86. In use, the user first grasps tab 94 and pulls, thereby peeling adhesive strips 92 from release liner 86. Adhesive strips 92 may then be easily applied to the desired site one at a time by the user. Release liner 86 is then removed from adhesive coated backing 82, and backing 82 is applied to the patient. Finally, the remaining portions of carrier layer 88 is removed from backing 82.

DETAILED DESCRIPTION

U.S. Pat. Nos. 3,645,835, and 4,595,001 describe methods of making high vapor/moisture permeable films and methods for testing their permeability. The film/adhesive composite should transmit moisture vapor at a rate of at least 300 g/m$^2$/24 hrs/37° C./100–10% RH. Preferably the adhesive coated film transmits moisture vapor at a rate of at least 700 g/m$^2$/24 hrs/37° C./100–10% RH, and more preferably above 2000 g/m$^2$/24 hrs/37° C./100–10% RH.

The backing is preferably conformable to anatomical surfaces. This means that when the composite is applied to an animal anatomical surface it conforms to the surface even when the surface is moved. The preferred backings are also conformable to animal anatomical joints. When the joint is flexed and then returned to its unflexed position, the backing stretches to accommodate the flexion of the joint but is resilient enough to continue to conform to the joint when the joint is returned to its unflexed condition.

Conformability is also somewhat dependent on thickness, thus the thinner the backing the more conformable it is. Generally, the films are from 12 to 25 microns thick. Examples of polymers which are suitable for use as wound dressing films in the present invention include polyurethane such as Estane™ (B. F. Goodrich, Cleveland, Ohio), elastomeric polyester such as duPont Hytrel™ polyester elastomer (Wilmington, Del.), polyethylene, blends of polyurethane and polyester, chlorinated polyethylene, styrene/butadiene block copolymers such as Kraton™ brand thermoplastic rubber (Shell Chemical Company, Houston, Tex.), Pebax™ polyether block amides (distributed by Rilsan Corp., Glen Rock, N.J.), ms and polyvinyl chloride.

Particularly preferred backings are elastomeric polyurethane, polyester films or polyether block amides. These films combine the desirable properties of resiliency, high moisture vapor permeability and transparency.

The preferred pressure-sensitive adhesives which can be used for the backing adhesive are the normal adhesives which are applied to the skin such as the acrylate copolymers described in U.S. Pat. No. Re. 24,906, particularly a 97:3 iso-octyl acrylate:acrylamide copolymer. Other useful adhesives are those described in U.S. Pat. No. 3,389,827, which discloses block copolymers having three or more polymer block structures having a general configuration -A-B-A- wherein each A block is a thermoplastic polymer with a glass transition temperature above room temperature (i.e., above about 20° C.) having an average molecular weight between about 5000 and 125,000 and the B block is a polymer of a conjugated diene having an average molecular weight between about 15,000 and 250,000. Additional examples of useful adhesives are iso-octyl acrylate/n-vinyl pyrrolidone copolymer adhesives and crosslinked acrylate adhesives such as, for example, those described in U.S. Pat. No. 4,112,213. Inclusion of medicaments or antimicrobial agents such as iodine in the adhesive is useful for reducing skin flora and preventing infection. U.S. Pat. Nos. 4,310,509 and 4,323,557 describe such antimicrobial adhesives.

Examples of materials suitable for use as liners and carrier layers in the present invention are liners made of kraft papers, polyethylene, polypropylene, polyester or composites of any of these materials. These liners are coated with release agents such as fluorochemicals or silicone. U.S. Pat. No. 4,472,480 describes low surface energy perfluorochemical liners. The preferred liners are papers, polyolefin films, or polyester films coated with silicone release materials. Examples of the silicone coated release papers are Polyslik™ silicone release papers supplied by James River Co., H. P. Smith Division (Bedford Park, Ill.), and silicone coated papers supplied by Daubert Chemical Co.(Dixon, Ill.). The preferred liner is 1-60BKG-157 paper available from Daubert, which is a super calandered kraft paper with a water based silicone surface.

Other combinations of adhesives and liners are feasible. Those skilled in the art are familiar with processes of testing a new adhesive against different liners or a new liner against different adhesives in order to arrive at the combination of qualities desired in the final product. Handbook of Pressure-Sensitive Adhesive Technology, Chapter 18 "Silicone Release Coatings" Van Nostrand-Reinhold, 1982, pp. 384–403 describes the considerations pertinent to selection of a silicone release liner. U.S. Pat. No. 4,472,480 describes considerations pertinent to selection of a perfluoropolyether release liner. In the preferred wound dressing embodiment of the present invention, the choice of adhesive is limited to those that are safe to use on skin, and preferably to those that are of the class known as hypoallergenic. The preferred acrylate copolymers are adhesives of this class. Liners are available from a variety of manufacturers in a wide variety of proprietary formulations. One normally tests these in simulated use conditions against an adhesive of choice to arrive at a product with the desired release characteristics.

Transparent dressings having a carrier layer for enhanced delivery are described in more detail in U.S. patent application Ser. No. 205,344, filed Nov. 10, 1980 by applicant, and entitled "Device and Method of Applying Conformable Thin Adhesive Coated Films," incorporated herein by reference.

The adhesive strips used in the present invention may be any adhesive strip appropriate for contact with human or animal surfaces to provide closure for wound sites or to secure catheter tubes, etc. Examples of adhesive strips of this type are, for example, Steri-Strip™ adhesive strips, Micropore™ tape, Transpore™ tape (all from 3M Company), foam tape and any of the other available medical tapes. The catheter support strip may be any structure provided on the film backing at one edge to enhance stability of the device. For example, the catheter support strip may be a film/adhesive laminate (or in other words an additional stripe of adhesive tape), an additional bead of adhesive or an additional bead of adhesive further enhanced by addition of fibers to the adhesive to provide some measure of rigidity and bulk for support. The adhesive of the catheter support strip may optionally have properties of greater adhesion to skin than the adhesive coated on the backing.

The composite of the present invention may be made by conventional techniques (e.g., extrusion, solvent casting, calendering, and laminating and the like) which are familiar to those skilled in the art. (See Modern Plastics Encyclopedia McGraw Hill, 1984–85; Coating and Laminating Machines, Weiss Coverting Technology Co., 1977.) The method of making a composite is further exemplified by the following non-limiting example.

EXAMPLE 1

A sample of Tegaderm™ transparent dressing was prepared as follows:

Twenty-five grams per square meter of an adhesive prepared in accordance with U.S. Pat. No. Re. 24,906, comprising a 97:3 units of iso-octyl acrylate: acrylamide copolymer was applied to a release liner of 78 pounds per ream (127 grams per meter squared) bleached, one-side coated, polyethylene and silicone paper (Polyslik S-8053, James River Co., H. P. Smith Division, Bedford Park, Ill.) utilizing a standard horizontal knife coater. A 1.1 mil (28 micron) film of "Estane 58309NAT022" polyurethane resin (B. F. Goodrich, Cleveland, Ohio) laminated to a carrier layer of 78 pounds per ream (127 grams per meter squared) bleached, one-side coated, polyethylene and silicone paper was laminated on its film side to the adhesive surface of the adhesive/liner laminate. The carrier layer was provided with a score line dividing the carrier into a central window portion surrounded by a separately removable frame portion. The release liner was temporarily removed from the adhesive and a strip of a backing/adhesive laminate prepared in accordance with U.S. Pat. No. 4,366,814 and commercially available from 3M Company as Steri-Strip™ adhesive strips was laminated to one edge of the above structure with the backing side of the Steri-Strip™ laminate adjacent to the adhesive side of the transparent dressing to form the permanent catheter support strip. The temporarily removed release liner was then relaminated to the exposed adhesive. Another Steri-Strip™ adhesive strip was then releasably adhered to the upper surface of the carrier across the entire width of the dressing so that it straddled the score line. Any overlapping adhesive strip material was then trimmed.

The foregoing description has been directed to particular preferred embodiments for purposes of illustration and explanation. Those skilled in the art will appreciate that many modifications will be possible without departing from the spirit of the invention. For example, the composite may further comprise adhesive voids to increase moisture vapor transmission.

We claim:

1. A wound treatment composite comprising
   a) a thin film backing,
   b) a pressure-sensitive adhesive coated on at least a portion of one surface of said backing,
   c) a release liner releasably adhered to the adhesive coated surface of the backing,
   d) at least one adhesive strip releasably adhered to the release liner on the opposite surface of the release liner from the backing, wherein said adhesive strip is provided with tab means for enhanced handleability and easy removal of the adhesive strip from the release liner.

2. The wound treatment composite of claim 1, wherein said release liner has separation means to provide separately removable release liner portions, and at least one adhesive strip is releasably adhered to the release liner across said separation means, such that one separately removable liner portion may be removed from said adhesive-coated backing together with said adhesive strip such that at least one free end of each adhesive strip is readily available for grasping by the user for delivery of the adhesive strip to the desired site.

3. The wound treatment composite of claim 2, wherein said separation means is a continuous-cut line.

4. The wound treatment composite of claim 2, wherein said separation means is a perforation line.

5. The wound treatment composite of claim 2, wherein said release liner is cut into a central portion and two side portions located on opposite sides of the central portion.

6. The wound treatment composite of claim 5, wherein at least one adhesive strip is attached to the central portion and both side portions of the release liner.

7. The wound treatment composite of claim 1, further comprising a catheter support strip.

* * * * *